United States Patent [19]

Singh et al.

[11] Patent Number: 5,510,371
[45] Date of Patent: Apr. 23, 1996

[54] INHIBITORS OF FARNESYL-PROTEIN TRANSFERASE

[75] Inventors: Sheo B. Singh, Edison; George M. Garrity, Westfield, both of N.J.; Olga Genillourd, Madrid, Spain; Russell B. Lingham, Watchung, N.J.; Isabel Martin, Madrid, Spain; Mary N. Omstead, E. Greenwich, R.I.; Keith C. Silverman, Somerset; Deborah L. Zink, Manalapan, both of N.J.

[73] Assignee: Merck & Co., Inc., Rahway, N.J.

[21] Appl. No.: 254,228

[22] Filed: Jun. 6, 1994

[51] Int. Cl.$^6$ .................... A61K 31/335; A61K 31/225
[52] U.S. Cl. .................... 514/450; 514/547; 549/267; 560/180; 560/181; 560/55; 560/60
[58] Field of Search .................... 549/267; 560/55, 560/60, 180, 181; 514/450, 547

[56] References Cited

U.S. PATENT DOCUMENTS

| 5,043,268 | 8/1991 | Stock | 435/15 |
| 5,141,851 | 8/1992 | Brown et al. | 425/15 |
| 5,245,061 | 9/1993 | Singh | 554/121 |
| 5,260,465 | 11/1993 | Singh et al. | 554/134 |
| 5,260,479 | 11/1993 | Singh | 560/190 |
| 5,276,217 | 1/1994 | Tius | 568/821 |

FOREIGN PATENT DOCUMENTS

| 0456180A1 | 11/1991 | European Pat. Off. |
| 0537007A1 | 4/1993 | European Pat. Off. |
| WO 91/16340 | 10/1991 | WIPO |

OTHER PUBLICATIONS

Bos, J. L. "ras Oncogenes in Human Cancer: A Review", Cancer Research, vol. 49, pp. 4682–4689 (1989).
Gibbs, J. B., "Ras C-Terminal Processing Enzymes New Drug Targets?", Cell, vol. 65, 1–4 (1991).
Gibbs, J. B. et al., "Selective Inhibition of Farnesyl–Protein Transferase Blocks Ras Processing in Vivo", The Journal of Biological Chemistry, vol. 268, No. 11, pp. 7617–7620. (1993).
Goldstein, J. L. et al., "Nonfarnesylated Tetrapeptide Inhibitors of Protein Farnesyltransferase", The Journal of Biological Chemistry, vol. 266, No. 24, pp. 15575–15578 (1991).
James, G. L. et al., "Benzodiazepine Peptidomimetics: Potent Inhibitors of Ras Farnesylation in Animal Cells", Sciences, vol. 260, pp. 1937–1942 (1993).
Kohl, N. E. et al., "Selective Inhibition of ras–Dependent Transformation by a Farnesyltransferase Inhibitor", Science, vol. 260, pp. 1934–1937 (1993).
Leftheris, K. et al., Peptide Based P21RAS Farnesyl Transferase Inhibitors: Systematic Modification of the Tetrapeptide CA1A2X Motif, (1994), Bioorganic & Medicinal Chemistry Letters, 4, No. 7, pp. 887–892.
Pompliano, D. L. et al., Steady–State Kinetic Mechanism of Ras Farnesyl: Protein Transferase, (1992), Biochemistry, 31 pp. 3800–3807.
Qian, Y et al., Design and Structural Requirements of Potent Peptidomimetic Inhibitors of p21ras Farnesyltransferase, (1994), The Journal of Biological Chemistry, 269, No. 17, pp. 12410–12413.
Reiss, Y. et al., Inhibition of Purified p21ras Farnesyl:Protein Transferase by Cys–AAX Tetrapeptides, (1990), Cell 62, pp. 81–88.
Reiss, Y et al., Sequence requirement for peptide recognition by rat brain p21 ras protein farnesyltransferase, (1991), Proc. Natl. Acad. Sci. USA, 88, pp. 732–736.
Schaber, M. D. et al., Polyisoprenylation of Ras in Vitro by a Farnesyl–Protein Transferase, (1990), The Journal of Biological Chemistry, 265, No. 25, pp. 14701–14704.
Singh, S. B. et al., "Fusidienol: A Novel Inhibitor of Ras Farnesyl–Protein Transferase from Fusidium griseum", Tetrahedron Letters, vol. 35, No. 27, pp. 4693–4696 (1994).
Kohl, N. E., et al., "Inhibition of farnesyltransferase induces regression of mammary and salivary carcinomas in ras transgenic mice," Nature Medicine, vol. 1, No. 8 (Aug. 1995).
Kohl, N. E. et al., "Protein farnesyltransferase inhibitors block the growth of ras–dependent tumors in nude mice", Proc. Natl. Acad, Sci. USA, vol. 91, pp. 9141–9145 (1994).

*Primary Examiner*—C. Warren Ivy
*Assistant Examiner*—Amelia Owens
*Attorney, Agent, or Firm*—David A. Muthard; Mark R. Daniel

[57] ABSTRACT

The present invention is directed to compounds which inhibit farnesyl-protein transferase (FPTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

20 Claims, No Drawings

INHIBITORS OF FARNESYL-PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J.Biol. Chem.* 263:18236 (1988); Farnsworth et al., *J. Biol. Chem.* 264:20422 (1989)).

Inhibition of Ras farnesylation in vivo has been demonstrated with lovastatin and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1989)). Cytosollocalized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In minor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et. al., ibid; Reiss etal., PNAS., 88:732–736 (1991)). Such inhibitors may inhibit while serving as alternate substrates for the Ras farnesyl-transferase enzyme, or may be purely competitive inhibitors (U.S. Pat. No. 5,141,851, University of Texas).

Recently, it has been demonstrated that certain inhibitors of farnesyl-protein transferase selectively block the processing of Ras oncoprotein intracellularly (N. E. Kohl et al. *Science*, 260:1934–1937 (1993) and G. L. James et al. *Science*, 260:1937–1942 (1993).

Citraconic acid derivatives, isolated as fermentation products from a strain of *Chaetomella acutiseta*, and synthetic analogs of those compounds have been described as inhibitors of farnesyl protein transferase (U.S. Pat. No. 5,260,465, EP-547671-A, U.S. Pat. Nos. 5,245,061 and 5,260,479).

It is, therefore, an object of this invention to develop non-peptide compounds which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes polyketide analogs which inhibit farnesyl-protein transferase and the farnesylation of the oncogene protein Ras, chemotherapeutic compositions containing the compounds of this invention, and methods for producing the compounds of this invention.

The compounds of this invention are illustrated by the following formulae:

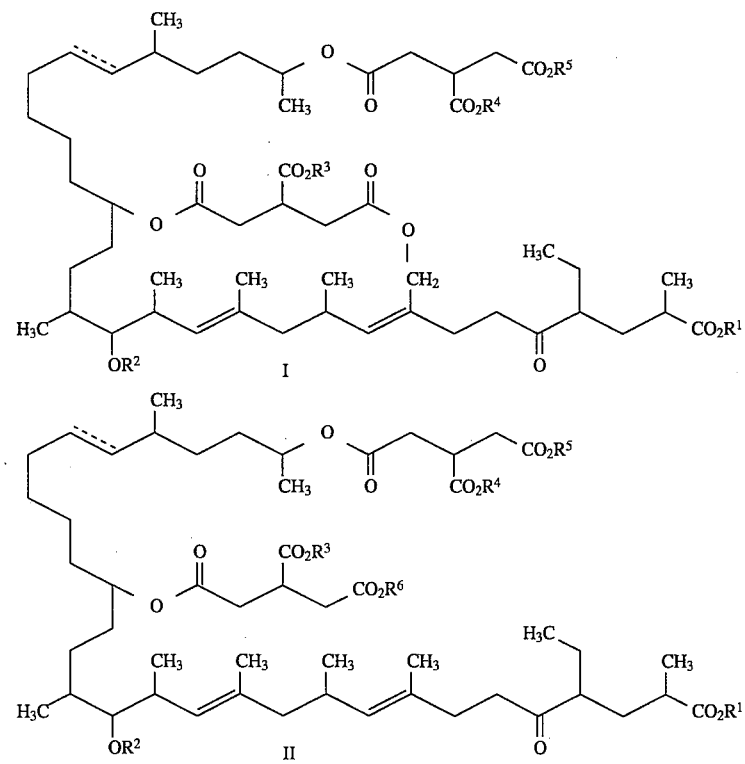

DETAILED DESCRIPTION OF THE INVENTION

The compounds of this invention are useful in the inhibition of farnesyl-protein transferase. In a first embodiment of this invention, the inhibitors of farnesyl-protein transferase are illustrated by the formula I:

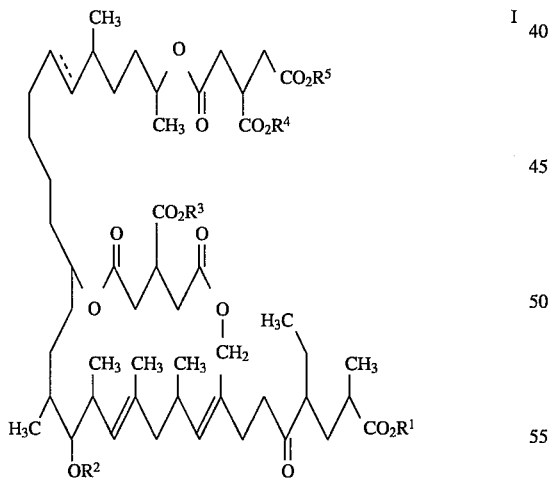

wherein:

$R^1$, $R^3$, $R^4$ and $R^5$ are independently selected from:
a) hydrogen;
b) $C_{1-5}$ alkyl; and
c) $C_{1-5}$ alkyl substituted with a member of the group consisting of:
i) phenyl,
ii) phenyl substituted with methyl, methoxy, halogen (Cl, Br, F, I) or hydroxy; and $R^2$ is selected from hydrogen, $C_{1-4}$ alkyl, benzoyl or acetyl;

wherein the dashed line represents the presence of a second bond, which results in a double bond, or the absence of a second bond; and wherein at least two $R^1$, $R^3$, $R^4$ or $R^5$ are hydrogen; or the pharmaceutically acceptable salts thereof.

In a second embodiment of this invention, the compounds are illustrated by the formula II:

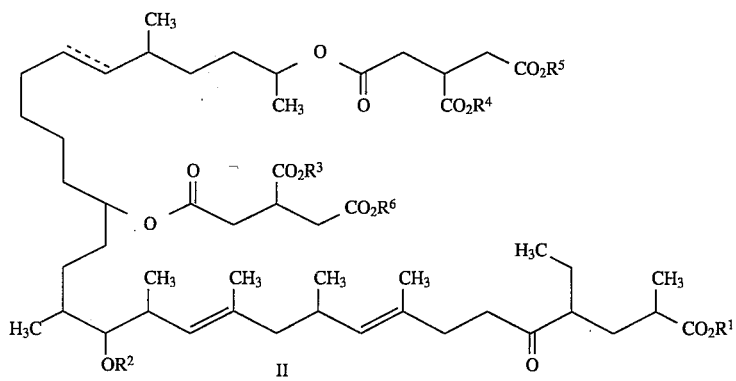

wherein:

R$^1$, R$^3$, R$^4$, R$^5$ and R$^6$ are independently selected from:
a) hydrogen;
b) C$_{1-5}$ alkyl; and
c) C$_{1-5}$ alkyl substituted with a member of the group consisting of:
i) phenyl,
ii) phenyl substituted with methyl, methoxy, halogen (Cl, Br, F, I) or hydroxy; and R$^2$ is selected from hydrogen, C$_{1-4}$ alkyl, benzoyl or acetyl;

wherein the dashed line represents the presence of a second bond, which results in a double bond, or the absence of a second bond; and wherein at least two R$^1$, R$^3$, R$^4$ or R$^5$ are hydrogen;
or the pharmaceutically acceptable salts thereof.

Another embodiment of the instant invention are prodrugs of the formula I hereinabove wherein:

R$^1$, R$^3$, R$^4$ and R$^5$ are independently selected from:
a) hydrogen;
b) C$_{1-5}$ alkyl; and
c) C$_{1-5}$ alkyl substituted with a member of the group consisting of:
i) phenyl,
ii) phenyl substituted with methyl, methoxy, halogen (Cl, Br, F, I) or hydroxy; and R$^2$ is selected from hydrogen, C$_{1-4}$ alkyl, benzoyl or acetyl; provided either one or none of R$^1$, R$^3$, R$^4$ or R$^5$ is hydrogen.

Still another embodiment of the instant invention are prodrugs of the formula II hereinabove wherein:

R$^1$, R$^3$, R$^4$ R$^5$ and R$^6$ are independently selected from:

a) hydrogen;
b) C$_{1-5}$ alkyl; and
c) C$_{1-5}$ alkyl substituted with a member of the group consisting of:
i) phenyl,
ii) phenyl substituted with methyl, methoxy, halogen (Cl, Br, F, I) or hydroxy; and R$^2$ is selected from hydrogen, C$_{1-4}$ alkyl, benzoyl or acetyl; provided either one or none of R$^1$, R$^3$, R$^4$, R$^5$ or R$^6$ is hydrogen.

In a preferred embodiment of this invention, the inhibitors of farnesyl-protein transferase are illustrated by the formula Ia:

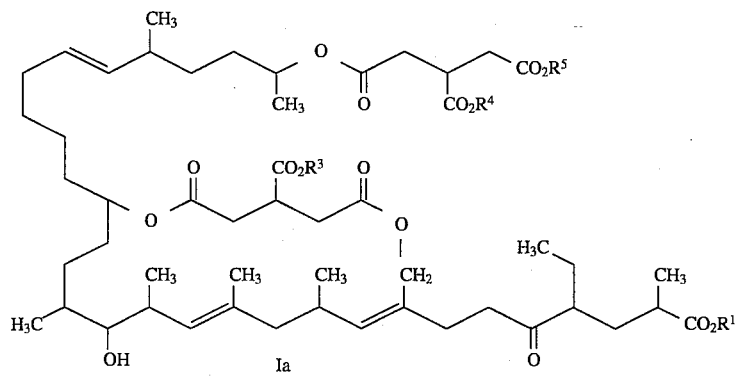

wherein:

R$^1$, R$^3$, R$^4$ and R$^5$ are independently selected from:
a) hydrogen;
b) C$_{1-5}$ alkyl; and
c) C$_{1-5}$ alkyl substituted with a member of the group consisting of:
i) phenyl,
ii) phenyl substituted with methyl, methoxy, halogen (Cl, Br, F, I) or hydroxy; and wherein at least R$^4$ and R$^5$ are hydrogen;
or the pharmaceutically acceptable salts thereof.

In a second preferred embodiment of this invention, the compounds are illustrated by the formula IIa:

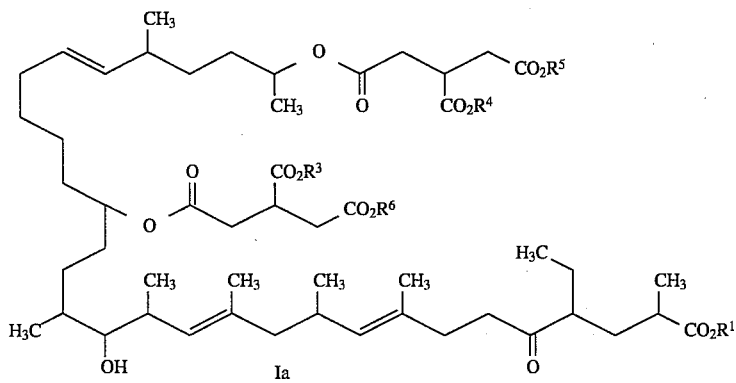

wherein: $R^1$, $R^3$, $R^4$, $R^5$ and $R^6$ are independently selected from:
a) hydrogen;
b) $C_{1-5}$ alkyl; and
c) $C_{1-5}$ alkyl substituted wth a member of the group consisting of:
i) phenyl,
ii) phenyl substituted with methyl, methoxy, halogen (Cl , Br, F, I) or hydroxy; and wherein at least $R^6$ and $R^3$ are hydrogen or $R^4$ and $R^5$ are hydrogen or $R^3$, $R^4$, $R^5$ and $R^6$ are hydrogen;
or the pharmaceutically acceptable salts thereof.

Still another preferred embodiment of the instant invention are prodrugs of the formulae Ia or IIa hereinabove wherein:

$R^1$, $R^3$, $R^4$, $R^5$ and $R^6$ are independently selected from:
a) $C_{1-5}$ alkyl; and
b) $C_{1-5}$ alkyl substituted wth a member of the group consisting of:
i) phenyl,
ii) phenyl substituted with methyl, methoxy, halogen (Cl , Br, F, I) or hydroxy.

The following are specific examples of the compounds of the instant invention:

1,2,3-propanetricarboxylic acid 1-[10-[4-carboxy 19-(6-carboxy-4-ethyl- 3-oxoheptyl)-12-hydroxy- 11,13,15, 17-tetramethyl-2,6-dioxo-1,7-dioxacycloeiocosa-14,18-dien-8-yl]-1,4-dimethyl-5-decenyl] ester; which is also known by the trivial name actinoplanic acid A:

1,2,3-propanetricarboxylic acid 1-[28-carboxy-11-[[3,4-dicarboxy- 1-oxopentyl]oxy]-26-ethyl-15-hydroxy-1, 4,14,16,18,20,22-heptamethyl-25-oxo-5,17,21-nonacosatrienyl] ester;
which is also known by the trivial name actinoplanic acid B:

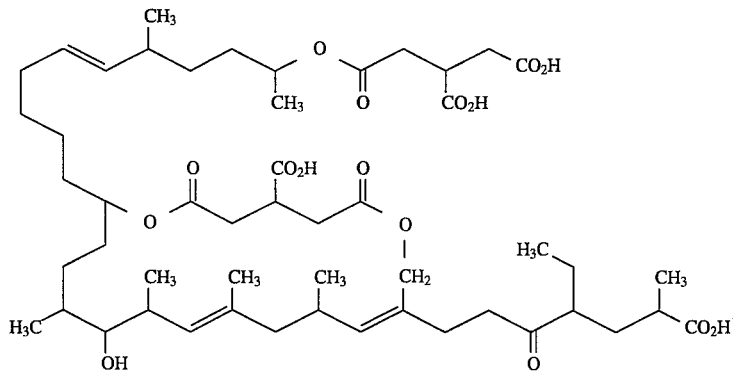

1 and

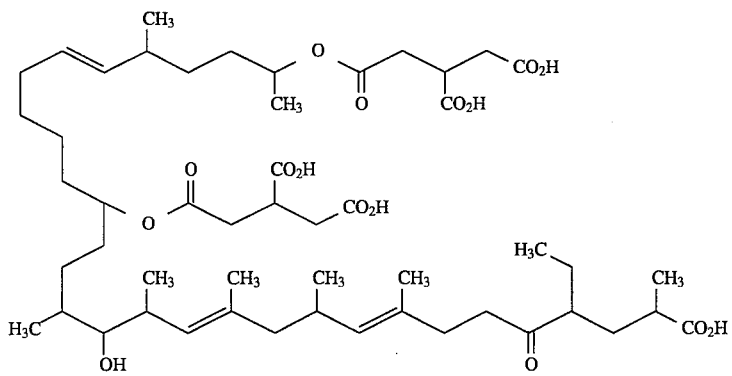

2

The following are specific examples of prodrugs of the compounds of the instant invention:

1,2,3-propanetricarboxylic acid 1-[10-[19-(4-ethyl-7-methoxy-6-methyl-3,7-dioxoheptyl)-12-hydroxy-11, 13,15,17-tetramethyl-4-(methoxycarbonyl)- 2,6-dioxo-1,7-dioxacycloeiocosa-14,18-dien-8-yl}-1,4-dimethyl-5-decenyl] 2,3-dimethyl ester

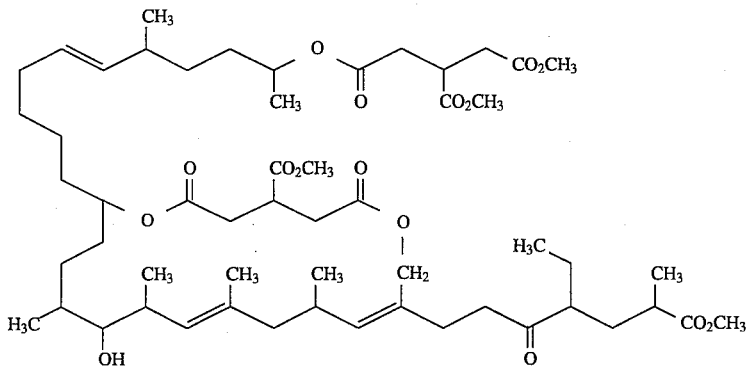

1,2,3-propanetricarboxylic acid 1-[26-ethyl-15-hydroxy-29-methoxy-11-[[5-methoxy-3-(methoxycarbonyl)-1, 5-dioxopentyl[oxy]-1,4,14,16,18,20,22,28-octamethyl-25,29-dioxo-5,17,21-nonacosatrienyl]2,3-dimethyl ester

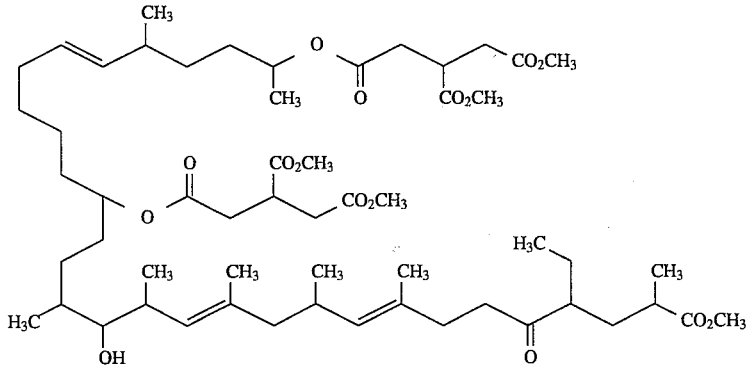

In the compounds of the present invention, combinations of substituents/or variables are permissible only if such combinations result in stable compounds.

As used herein, "alkyl" is intended to include both branched and straight-chain saturated aliphatic hydrocarbon groups having the specified number of carbon atoms. The term "alkyl" includes methyl, ethyl, propyl, iso-propyl, butyl, sec-butyl, tert-butyl and the like.

The pharmaceutically acceptable salts of the compounds of this invention include the conventional non-toxic salts of the compounds of this invention as formed, e.g., from non-toxic inorganic or organic bases. For example, such conventional non-toxic salts include those derived from inorganic bases such as sodium, potassium, calcium, magnesium, zinc, ammonium and the like; and the salts prepared from organic bases such as alkylammonium salts such as tetramethylammonium, tetrabutylammonium, choline, triethylhydroammonium, meglumine, triethanolhydroammonium, and the like.

The pharmaceutically acceptable salts of the compounds of this invention can be synthesized from the compounds of this invention which contain at least one carboxylic acid moiety by conventional chemical methods. Generally, the salts are prepared by reacting the instant compound with stoichiometric amounts or with an excess of the desired salt-forming inorganic or organic base in a suitable solvent or various combinations of solvents.

The compounds 1 and 2 may be prepared in an aerobic fermentation procedure employing a novel culture, MA7066, identified as Actinoplanes sp. Although the use of this organism is specifically described herein, mutants of the above described organism are also capable of producing the compounds of this invention.

The culture MA7066 is that of an actinomyces, Actinoplanes sp., isolated from a lichen growing on an oak tree at La Haruela, Madrid, Spain. This culture has been deposited with the American Type Culture Collection at 12301 Parklawn Drive, Rockville, Md. 20852 as ATCC 55532.

The following is a general description of culture MA7066:

Chemotaxonomic characteristics—MA7066 contained meso-diaminopimelic acid in the peptidoglycan. Whole cell sugars were rhamnose and galactose. Major whole cell fatty acids were $17:0_{anteiso}$, 15:0, $16:0_{iso}$, $15:0_{iso}$, 17:1 cis 9, $17:1_{iso}$ C, $17:0_{iso}$, $17:1_{anteiso}$, 18:1 cis 9 and $16:1_{iso}$ H. Specific quantities are listed in Table 1.

General growth characteristics—Actinoplanes sp. MA7066—Good growth was obtained on yeast-malt extract agar, glycerol-asparagine agar, inorganic salts-starch agar, oatmeal agar, Czapek's agar, sucrose-nitrate-yeast extract agar and Sabouraud's maltose agar. Poor growth was observed on tap-water/NZ-Amine A agar. No growth on trypticase-soy agar.

Colony morphology—(On yeast-malt agar at 21d) Actinoplanes sp. MA7066—Substrate mycelium is a dark yellow brown, colony surface is orange with brown edges. No aerial growth. Globose sporangia were observed. Colonies are opaque, raised and have entire edges. The colonies are rubbery in texture and have a matte surface. Greater detail is provided in Table 3.

Micromorphology—Actinoplanes sp. MA7066—Vegetative mycelia (0.38–0.57 µm) give rise to sporangia on yeast-malt agar, Czapek's agar and sucrose-nitrate yeast extract agar. Sporangia are globose to ovoid and approximately 2.28×3.04 µm in size. Scant aerial growth was observed on Czapek's agar and tap-water agar. Very small numbers of motile spores were observed on occasion when mature cultures were flooded with sterile tap water.

Miscellaneous physiological reactions—Actinoplanes sp. MA7066Culture does not produce $H_2S$ in peptone-iron agar. Melanoid pigments were not formed in peptone-iron agar and tryptone-yeast extract broth. Starch was weakly hydrolyzed. Carbon source utilization pattern is shown in Table 2.

Diagnosis—Actinoplanes sp. MA7066—Cell wall analysis reveals that this culture has a type II cell wall but the whole cell sugar pattern that was observed is not consistent for members of this genus. Morphological studies showed that this culture produces zoospores in globose to ovoid sporangia but the sporangium is smaller than those of previously reported species. Comparison of the fatty acid profiles of this culture with those of the validly named species of Actinoplanes places this MA7066 in a cluster with *Actinoplanes deccannesis, A. brasiliensis, A. teichomyceticus, A. yunnanensis*, and *Couchiplanes caeruleus* (formerly *Actinoplanes caeruleus*). MA7066 can be differentiated from each of these species based upon morphological, chemotaxonomic and/or biochemical characteristics. Therefore, this culture is believed to be a novel species. Assignment to the genus Actinoplanes is based upon gross morphological characteristics and overall similarity in fatty acid composition. As cell wall composition differs from the validly named species, it is likely that MA7066 may form the nucleus of a previously unrecognized genus. Determination of proper placement will require additional studies, including phylogentic analysis.

The compound 1 may also be prepared in an aerobic fermentation procedure employing a novel culture, MA7099, identified as Streptomyces sp. Although the use of this organism is specifically described herein, mutants of the above described organism are also capable of producing the compounds of this invention.

The culture MA7099 is that of a bacterium, Streptomyces sp, isolated from a soil sample collected in Naiguata, Venezuela. This culture has been deposited with the American Type Culture Collection at 12301 Parklawn Drive, Rockville, Md. 20852 as ATCC 55550.

The following is a general description of culture MA7099:

Chemotaxonomic characteristics—The peptidoglycan of MA7099 contained LL-diaminopimelic acid. Major whole cell fatty acids were $16:0_{iso}$, $15:0_{iso}$, $17:1_{iso}$ C, $17:0_{iso}$, $14:0_{iso}$, $15:0_{anteiso}$, $16:1_{iso}$ H, 16:1 cis 9, 16:0 and $17:0_{anteiso}$. Specific quantities are listed in Table 1.

General growth characteristics—Streptomyces sp. MA7099—Good growth was obtained on yeast-malt extract agar, glycerol-asparagine agar, inorganic salts-starch agar, oatmeal agar, Czapek's sucrose nitrate agar, trypticase-soy agar and Sabouraud's maltose agar. Poor growth was observed on tap-water/NZ-Amine A agar. Growth occurred at 27° and 37° C.

Colony morphology—(On yeast-malt agar at 21d) Streptomyces sp. MA7099—Substrate mycelium is a light yellow-brown. Aerial spore mass is abundant and white in color with numerous black patches. Colonies are opaque, raised and lobate. The colonies are rubbery in texture and have a matte surface. Greater detail is provided in Table 3.

Micromorphology—Streptomyces sp. MA7099—Aerial mycelia (0.57 µm) arise from substrate mycelia and are branched and flexous. In mature cultures (7–28d p.i.) the aerial mycelium terminates in chains of spores that occur as short, tightly coiled spirals. Sporulation occurs on YME, inorganic salts-starch agar, oatmeal, glycerol asparagine agar, and Czapek's agar. The aerial spore mass coalesces extensively on all but Czapek's agar.

Miscellaneous physiological reactions—Streptomyces sp. MA7099—Culture does not produce $H_2S$ in peptone-iron agar. Melanoid pigments were not formed in peptone-iron agar and tryptone-yeast extract broth. Starch was moderately hydrolyzed. Carbon source utilization pattern is shown in Table 2.

Diagnosis—Streptomyces sp. MA7099—Cell wall analysis reveals that this culture has a type I cell wall. Morphological studies reveal that the culture produces tightly coiled chains of spores that arise from the aerial mycelium. Upon aging, the aerial spore mass coalesces. These are characteristics typical for strains of Streptomyces. A comparison of the phenotypic data of MA7099 with that of the validly published species of Streptomyces in the taxonomic literature (1–7) shows that this strain bears a strong resemblance to Streptomyces violaceusniger. Comparison of the gas chromatographic profile of whole cell fatty acids of this culture to those contained within the MIDI Actinomycete Library (Version 3.70) showed a good match with Streptomyces violaceusniger. Based upon these results, Streptomyces sp. MA7099 is believed to be a novel strain of this species.

Observations of growth, general cultural characteristics and carbon source utilization were made in accordance with the methods of Shirling and Gottleib (Internat. J. System. Bacteriol. 16:313–340). Chemical composition of the cells was determined using the methods of Lechevalier and Lechevalier (in Actinomycete Taxonomy, A. Dietz and D. W. Thayer, Ed. Society for Industrial Microbiology, 1980). Whole cell fatty acids were derivatized and analyzed as methyl esters (FAMEs) by gas chromatography by the procedure of Miller and Berger using a MIDI Microbial Identification System (Microbial Identification Systems, Newark Del.). Coloration of the culture was determined by comparison with color standards contained in the Inter-Society Color Council-National Bureau of Standards Centroid Color Charts (US Dept. of Commerce National Bureau of Standards supplement to NBS Circular 553, 1985).

TABLE 1

Major Whole Cell Fatty Acids Found in Strains MA7099 and MA7066

| Fatty acid | MA7099 | MA7066 |
| --- | --- | --- |
| 14:0 iso | 6.43 | 0.91 |
| 15:0 iso | 22.72 | 14.78 |
| 15:0 anteiso | 5.77 | 20.57 |
| 16:1 iso H | 5.34 | 2.01 |
| 16:0 iso | 29.49 | 20.36 |
| 16:1 cis 9 | 4.37 | 1.28 |
| 16:0 | 2.89 | 0.51 |
| 17:1 iso C | 8.10 | 3.11 |

TABLE 1-continued

Major Whole Cell Fatty Acids Found in Strains MA7099 and MA7066

| Fatty acid | MA7099 | MA7066 |
| --- | --- | --- |
| 17:1 anteiso C | 1.16 | 2.82 |
| 17:0 iso | 7.18 | 3.07 |
| 17:0 anteiso | 2.47 | 21.29 |
| 17:1 cis 9 | 0.44 | 4.80 |
| 18:1 cis9 |  | 2.06 |

TABLE 2

Carbon Source Utilization Pattern of Strains MA7099 and MA7066

| Carbon source | MA7099 | MA7066 |
| --- | --- | --- |
| D-arabinose | 3 | 3 |
| L-arabinose | 3 | 3 |
| D-fructose | 3 | 2 |
| inositol | 3 | 3 |
| α-D-lactose | 3 | 3 |
| β-D-lactose | 3 | 3 |
| D-maltose | 3 | 3 |
| D-mannitol | 3 | 3 |
| D-mannose | 3 | 3 |
| D-raffinose | 3 | 2 |
| L-rhamnose | 3 | 3 |
| sucrose | 3 | 3 |
| D-xylose | 3 | 2 |
| α-D-glucose (control) | 3 | 3 |

3 = good utilization, 2 = moderate utilization, 1 = poor utilization 0 = no utilization

TABLE 3

Cultural Characteristics of MA7099 and MA7066

| | Amount of Growth | | Aerial Mycelium | | Soluble Pigments | | Substrate Mycelium | |
| --- | --- | --- | --- | --- | --- | --- | --- | --- |
| Medium | MA7099 | MA7066 | MA7099 | MA7066 | MA7099 | MA7066 | MA7099 | MA7066 |
| Yeast Extract Malt Extract | good | good | White (263 White), and black (267 Black). Spirals, completely coalesced | No aerial growth, brownish black surface (65 br Black). Sporangia present | none | none | Light yellow brown (76 l. y Brown) | Dark yellow brown ((78 d. y Br) |
| Glucose Asparagine | good | good | Medium gray (265, med Gy) with black (267 Black) patches. Spirals, coalesced | No aerial growth, medium orange surface (53 m. O). No sporangia | none | none | Pale yellow (89 p.Y) | Medium orange (53 m O) |
| Inorganic Salts-Starch | good | good | Black (267 Black) with white (263 White) edges. Spirals, coalesced. | No aerial growth, brownish black surface (65 br Black). No sporangia. | none | none | Yellow white (92 y White) | Brownish black (65 br Black) |
| Oatmeal | good | good | Black (267 Black) with white (263 White) areas. Spirals, coalesced. | No aerial growth, light brown surface (57 l.BR). No sporangia. | none | none | Light gray (264 l. Gray) | Light brown (57 l. Br) |
| Tap Water | fair | fair | Black (267 Black). Spirals, coalesced. | No aerial growth, yellow white surface (92 y White). No sporangia | none | none | Yellow white (92 y White) | Yellow white (92 y White) |
| Czapek | good | good | White (263 White), and medium gray (265 med Gy). Spirals. | Scant aerial hyphae, light yellow brown surface (76 l. y Br). Few sporangia | none | none | Yellow white (92 y White) | Light yellow brown surface (76 l. y Br). |
| Peptone Iron | good | good | | | none | none | | |

Compounds of this invention can be obtained by culturing the above noted microorganism in aqueous nutrient media containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, casein acid hydrolysate, corn steep liquor, distillers solubles, malt extracts and the like. Inorganic nitrogen sources such as ammonium salts (e.g. ammonium nitrate, ammonium sulfate, ammonium phosphate, etc.) can also be used. The various sources of nitrogen can be used alone or in combination in amounts ranging between 0.2 to 50 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as propylene glycol (P-2000®), polyalkylene glycol, polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organism which serves as seed in the production of the active compounds. After inoculation, the flasks are incubated with agitation at temperature ranging from 20° to 30° C., preferably 25° to 28° C. Agitation rates may range up to 400 rpm, preferably 200 to 220 rpm. Seed flasks are incubated over a period of 2 to 10 days, preferably 2 to 5 days. When growth is plentiful, usually 2 to 5 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 4 to 10 days. The fermentation is conducted aerobically at temperatures ranging from 20° to 40° C. To obtain optimum results, the temperatures are in the range of 22° to 28° C., most preferably 25° to 28° C. The pH of the nutrient medium suitable for producing the active compounds is in the range of 3.5 to 8.5, most preferably 5.0 to 7.5. After the appropriate period for production of the desired compound, fermentation flasks are harvested and the active compound(s) isolated.

A mixture of an alcoholic solvent and an oxygenated solvent, such as an ester or a ketone, is employed to extract a compound(s) of this invention from the fermentation medium.

The mixture is vigorously stirred and filtered, and the filtrate is concentrated under reduced pressure. Water is added to the concentrate and the pH is adjusted to about 3 with a mineral acid. The aqueous concentrate is then repeatedly extracted with a water immiscible oxygenated solvent. The water immiscible organic layer is removed and evaporated to dryness. The residue is then generally subjected to several separation steps such as adsorption and partition chromatography, and precipitation. For each separation step, fractions are collected and combined based on results from an assay and/or HPLC/TLC analysis.

The preferred solvent for extraction of the solid fermentation is a 1:1 mixture of methanol and 2-butanone. After concentrating the initial extract and diluting with water, the preferred partitioning solvent is dichloromethane.

The chromatographic separations may be carried out by employing conventional column chromatography with ionic or nonionic absorbents or resins. Silica gel, such as that available from E. Merck, is the preferred adsorbent. When silica gel is the adsorbent, an alcohol/chlorohydrocarbon/organic acid mixture such as methanol/chloroform/acetic acid/water is useful as an eluant. For reverse phase chromatography, the preferred adsorbent is a C8 bonded phase silica gel. The preferred eluant for reverse phase chromatography is a mixture of acetonitrile and water buffered at a low pH, such as 0.1% phosphoric acid, or trifluoroacetic acid. Ionic resins such as Dowex-1 (Cl−) or Dowex-50 ($Ca^{++}$) are also useful in the purification.

Reactions used to generate the compounds of this invention are prepared by employing reactions as shown in the Reaction Schemes 1 and 2, in addition to other standard manipulations such as ester hydrolysis, cleavage of protecting groups, etc., as may be known in the literature or exemplified in the experimental procedures.

These reactions may be employed in a linear sequence to provide the compounds of the invention.

Synopsis of reaction Schemes 1∝2:

As shown in Reaction Scheme 1, the tetracarboxylic acid or corresponding ester(s) of the formula Ib may be hydrogenated under limiting conditions in the presence of an appropriate catalyst, such as 5% Pd/C and the like, to provide the reduced compound Ic of the instant invention wherein the secondary double bond has been reduced. Treatment of the compound of the formula Ib with a suitable alkylating agent, such as an alkyl halide, such as methyl iodide, ethyl iodide and the like, in the presence of a mild base, such as sodium hydride and the like, provides the corresponding alkyl ether Id. Similarly, reaction of compound Ib with a suitable acetylating or aroylatying agent, such as acetyl chloride, benzoyl chloride and the like, in the presence of a suitable mild base provides the corresponding alkyl or aryl carbonyloxy compound Ie.

The same reactions are generally applicable to derivatization of the pentacarboxylic acid and corresponding ester(s) as shown in Reaction Scheme 2.

REACTION SCHEME 1
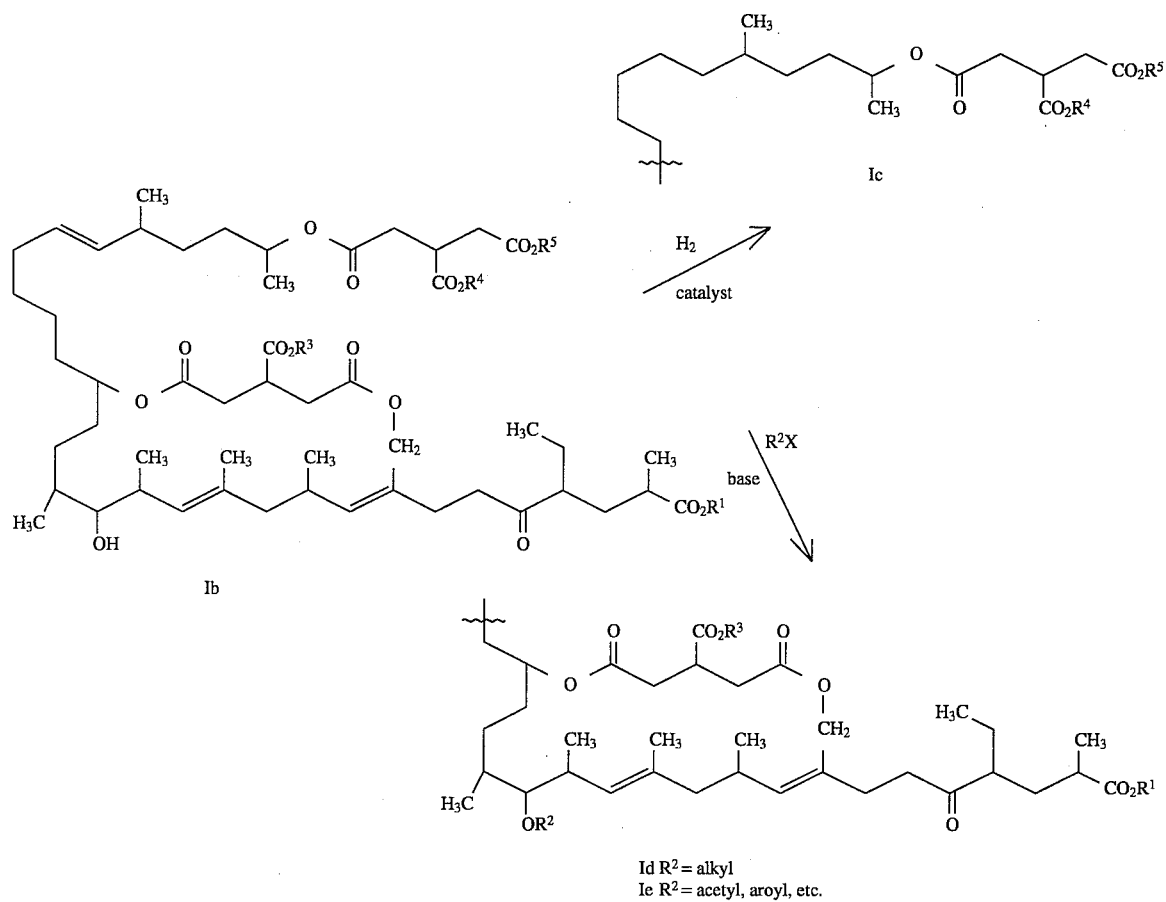
REACTION SCHEME 2
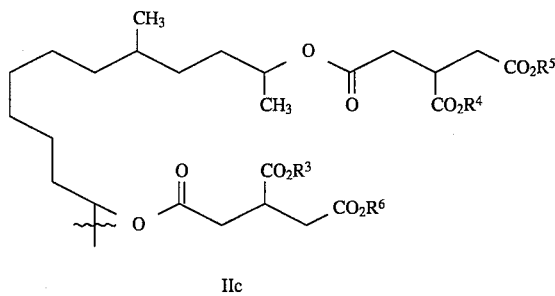

-continued
REACTION SCHEME 2

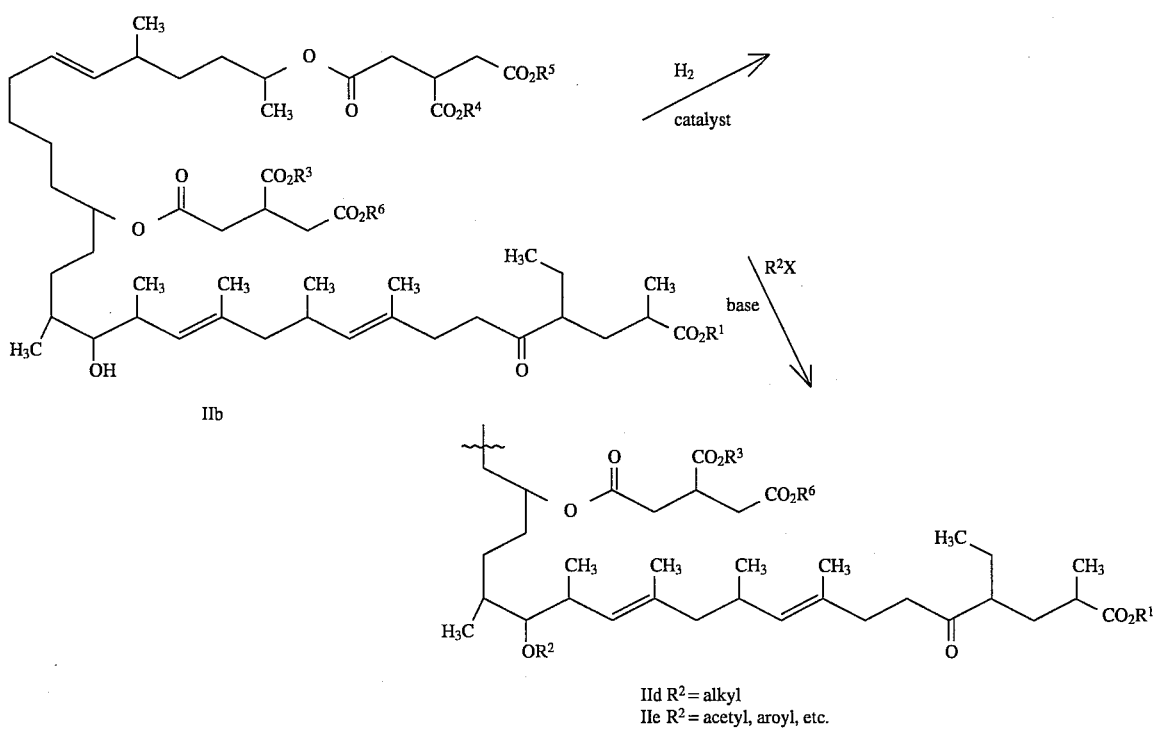

IId $R^2$ = alkyl
IIe $R^2$ = acetyl, aroyl, etc.

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carders or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carders which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carders, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of Compounds 1 and 2 by Fermentation of MA7066
A. Culturing MA 7066
Frozen vegetative mycelia supported on nutrient medium agar plugs were spread over BAM2 nutrient agar plates, which were incubated at 28° C. for 7–10 days. BAM2 nutrient consists of yeast extract 1 g, beef extract 1 g, casein hydrolysate 2 g, glucose 10 g and agar 15 g in 1 liter of distilled water which was adjusted to pH 7.2 with NaOH. Resulting growth was used to inoculate 50 ml of aqueous ATCC medium (formulation below), that was incubated at 28° C. for 96 hours. 1 ml of culture suspension was added to 1 ml of 20% (wt/v) glycerol in 4 ml screw cap glass vials and stored at −80° C. 1 ml of culture suspension was used to inoculate agar slants for Culture Collection preparation and storage of lyophilized ampules.

A seed culture was produced by inoculating 50 ml of aqueous ATCC nutrient medium in a 250 ml triple baffled Erlenmeyer flask with 2 ml of thawed frozen vegetative mycelia. ATCC nutrient medium consisted of glucose 10 g, soluble starch 20 g, yeast extract 5 g, N-Z amine E 5 g, $CaCO_3$ 1 g, beef extract 3 g, and Bacto-peptone 5 g in 1 liter distilled water, adjusted to pH 7.0 with NaOH prior to $CaCO_3$ addition. The culture vessel was incubated at 28° C. and shaken at 220 rpm for 96 hours in order to obtain sufficient biomass for use as an inoculum for production medium. 2 ml of seed culture was aseptically transferred to 44 ml of KS production medium in a 250 ml non-baffled Erlenmeyer flask.

The production medium contained dextrin 30 g, primary yeast 10 g, soybean meal 5 g, tomato paste 7.5 g, and $CoCl_2.6H_2O$ 5 mg in 1 liter of distilled water, adjusted to pH 7.3 with NaOH. The production medium was incubated at 28° C. and shaken at 220 rpm for 120 hours prior to harvest.

* Two additional production media were found to give comparable and/or superior RASIT results when utilized.
KHC production medium contained dextrin 20 g, B-cyclodextrin 10 g, primary yeast 10 g, tomato paste 20 g, and $CoCl_2.6H_2O$ 5mg in 1 liter distilled water, adjusted to pH 7.2 with NaOH.
RAM-3 production medium contained mannitol 30 g, soluble starch 10 g, soybean meal 20 g, and Bacto yeast extract 10 g in 1 liter distilled water, adjusted to pH 7.0 with NaOH.
The seed culture used as inoculum for KHC and RAM-3 production media was obtained as described above.

EXAMPLE 2

Preparation of Compound 2 by Fermentation of MA 7099
A. Culturing MA 7099

Culture MA 7099 was maintained as a confluent matte of vegetative and aerial mycelia and spores coveting the surface of YME or YMETE agar media (plates or slants). YME medium consists of: yeast extract, 4.0 g/L; malt extract, 10.0 g/L; and dextrose, 4.0 g/L. YMETE medium is identical to YME but includes the addition of 10 ml/L of a trace element solution (prepared in 0.6N HCl and containing in g/L: $MgSO_4.7H_2O$, 61.1; $CaCO_3$, 2.0; $FeCl_3.6H_2O$, 5.4; $ZnSO_4.7H_2O$, 1.44; $MnSO_4.H_2O$, 1.11; $CuSO_4.5H_2O$, 0.25; $CoCl_2.6H_2O$, 0.28; $H_3BO_3$, 0.062; and $Na_2MoO_4.2H_2O$, 0.49). Fully mature slants or plates are stored at 4C until ready for use. Seed cultures were inoculated using a sterile transfer tube to facilitate aseptic transfer of a plug cut from the grown agar plate into either of two types of seed vessels: a 25×150 mm glass test tube containing a glass cover slip insert and 12 mls seed medium or a 3-baffled 250 mls Erlenmeyer flask containing 50 mls of seed medium of the following composition (in g/liter); dextrose, 1.0; dextrin, 10.0; beef extract (Difco), 3.0; ardamine PH, 5.0; and NZ amine type E (Sheffield), 5.0; $MgSO_4.7H_2O$, 0.05; $CaCO_3$, 0.5; and 2.0 mls mixed sodium and potassium phosphate buffer (pH 7.0). The pH of the seed medium was adjusted to 7.0–7.2 by addition of NaOH before addition of the $CaCO_3$ component. Seed medium was prepared using distilled water, dispensed into Erlenmeyer flasks that were capped with cotton plugs or stainless steel capped glass test tubes before being autoclaved at 121° C. for 20 minutes. Seed cultures were incubated at 28° C., on a gyrotory shaker (220 rpm, 5.1 cm throw) for 52 hours prior to inoculation of fermentation flasks.

Fermentations were performed on liquid and solidified production medium formulated as follows (in g/L): cerelose, 75.0; lard water, 22.0; whey, 15.0; ardamine PH, 10.0; $CaCl_2$, 2.0; $MgSO_4.7H_2O$, 1.0; and $COCl_2.6H_2O$, 0.00015. Solidification of production medium was accomplished by addition of 15 g/L agar. Production medium vessels were capped with cotton plugs and sterilized at 121° C. for 20 minutes. Liquid production flasks were inoculated with 2.5 ml vegetative seed growth; solidified production flasks were inoculated with 1.5 ml seed growth applied to the solid surface. Liquid production flasks were incubated on a gyrotory shaker (220 rpm, 5.1 cm throw) at 28° C.; solidified production flasks were incubated without agitation at 28° C. Liquid flasks were sampled at 7 days and then returned to the incubator. All flasks were harvested following 15 day fermentation.

EXAMPLE 3

Isolation of actinoplanic acid A (1) and B (2) from MA7066 (Actinoplanes sp.):

The fermentation broth (4 L) of culture MA7066 (ATCC 55532) grown on a liquid medium was filtered through a bed of Celite and the filtrate (pH 7.3) was concentrated to a volume of one liter. The solution was cooled to 0° C. and was acidified to pH 1.5 by dropwise addition of concentrated hydrochloric acid while stirring. The acidified solution was extracted with ethyl acetate (2×1.0 L). The ethyl acetate extract was concentrated under reduced pressure to give 7.0 g of dark gum which was triturated with methanol (60 mL) and filtered. The filtrate was chromatographed on a Sephadex LH-20 column (2.0 L) packed in methanol and the column was eluted with methanol. The active fraction (330 mg) eluted in a broad band between 0.94–1.18 L of elution volumes of methanol. The combined active fractions were split into four portions which were each chromatographed on a Zorbax RX C-8 (22×250 mm) HPLC column and eluted with 55% aqueous acetonitrile containing 0.3% trifluoroacetic acid at a flow rate of 7 mL per minute for 30 minutes followed by 8 mL per minute. Actinoplanic acid A (1) was eluted between 41 to 47 minutes followed by actinoplanic acid B (2) between 50 to 58 minutes. The resulting fractions were combined to give actinoplanic acid A (1) and actinoplanic acid B (2) both as a gum. Purity of the compounds was verified by HPLC on a complimentary Zorbax RX C-8 analytical column (4.6×250 mm) eluting with 70% aqueous-acetonitrile containing 0.3% TFA. Actinoplanic acid A (1) eluted at $t_R$ 4.99 min and B (2) at $t_R$ 5.53 minutes.

EXAMPLE 4

Isolation of Actinoplanic acid B from MA7099 (Streptomyces sp.)

The fermentation broth of MA7099 (2.3 L) was filtered through Celite and the filtrate was freeze dried to give semi-solid which was suspended in 120 mL methanol. The solid was removed by filtration and the filtrate was chromatographed on a 2.0 L Sephadex LH-20 column eluted with methanol. The FPTase active fraction (1.0 g) was eluted between 0.97 to 1.2 L elution volume of methanol. An aliquot (25%) of this fraction was chromatographed on a reverse phase Zorbax RX C-8 HPLC column (22×250 mm) and eluted (8 mL per minute) with 30% aqueous acetonitrile containing 0.1% TFA for 60 minutes. The newly collected active fraction was rechromatographed on a reverse phase Zorbax RX C-8 HPLC column (4.6×250 mm) and eluted at 50° C. with 70% aqueous acetonitrile containing 0.1% TFA at a flow rate of 1 mL per minute to give a compound which was identical to actinoplanic acid B (2) isolated from MA7066. The identity was confirmed by HPLC and FABMS.

Physical properties of actinoplanic acids A and B:
Actinoplanic acid A ( 1 ):
  $[\alpha]_D^{25}$ 23 (C, 0.13, $CH_3OH$)
  FABMS (+) m/z 949 ([M+H]), 971 ([M+Na]), 987 ([M+K]). (−) m/z 947 ([M−H])
  HR-FAB: (+) 971.5389 (calcd. for $C_{51}H_{80}O_{16}$+Na: 971.5344).
  IR (ZnSe) $v_{max}$: 3600–2600 (broad), 2932, 1713, 1450, 1379, 1250, 1177, 967 $cm^{-1}$.

TABLE 4

NMR assignment of Actinoplanic acid A (1) in $CD_3OD$.

| # | δC | Type | δH* |
|---|----|------|-----|
| 1 | 215.50 | CO | |
| 2 | 180.0 | CO | |
| 3 | 176.80 | CO | |
| 4 | 175.20 | CO | |
| 5 | 175.00 | CO | |
| 6 | 174.90 | CO | |
| 7 | 173.00 | CO | |
| 8 | 172.30 | CO | |
| 9 | 137.30 | CH | 5.25, dd, J = 15.5, 8 |
| 10 | 136.90 | CH | 5.18, brd, J = 8 |
| 11 | 134.50 | C | |
| 12 | 133.30 | C | |
| 13 | 131.30 | CH | 4.84 |
| 14 | 130.10 | CH | 5.35, td J = 6.5, 15.5 |
| 15 | 82.10 | CH | 3.05, dd, J = 10, 1.0 |
| 16 | 76.80 | CH | 4.72, m |
| 17 | 73.00 | CH | 4.86 |
| 18 | 62.80 | CH2 | 4.93, dJ = 13 |
| | | | 4.44, d, J = 13 |
| 19 | 52.50 | CH | 2.57, m |
| 20 | 50.30 | CH2 | 2.18, quintet, J = 7.5 |
| | | | 1.86 |
| 21 | 41.70 | CH2 | 2.68 |
| | | | 2.54 |
| 22 | 39.30 | CH | 3.20, t, J = 7.5 |
| 23 | 39.10 | CH | 2.26, m |
| 24 | 38.70 | CH | 3.16, quintet, J = 6.5 |
| 25 | 38.10 | CH | 2.04, quintet, J = 6.5 |
| 26 | 37.90 | CH2 | 2.42, dd, J = 15.5, 10 |
| | | | 2.70, m |
| 27 | 37.70 | CH | 2.53 |
| 28 | 37.00 | CH | 1.62 |
| 29 | 36.70 | CH2 | 2.68 |
| | | | 2.57 |
| 30 | 36.60 | CH2 | 2.82 |
| | | | 2.53 |
| 31 | 36.10 | CH2 | 2.72 |
| | | | 2.54 |
| 32 | 35.90 | CH2 | 1.67 |
| | | | 1.67 |
| 33 | 34.90 | CH2 | 2.52 |
| | | | 1.51 |
| 34 | 34.00 | CH2 | 1.50 |
| | | | 1.33 |
| 35 | 33.80 | CH2 | 1.62 |
| | | | 1.20 |
| 36 | 33.40 | CH2 | 1.96 |
| | | | 1.96 |
| 37 | 32.70 | CH2 | 1.26 |
| | | | 1.26 |
| 38 | 30.70 | CH | 2.70 |
| 39 | 30.50 | CH2 | 1.34 |
| | | | 1.34 |
| 40 | 29.50 | CH2 | 2.37, dd, J = 14.5, 7 |
| | | | 2.14, dd, J = 13.5, 1.2 |
| 41 | 26.70 | CH2 | 1.31 |
| | | | 1.00 |
| 42 | 26.40 | CH2 | 1.59 |
| | | | 1.41 |
| 43 | 25.70 | CH2 | 1.36 |
| | | | 1.27 |
| 44 | 23.20 | CH3 | 0.88, d J = 7 |
| 45 | 21.50 | CH3 | 0.94, d, J = 6.5 |
| 46 | 20.20 | CH3 | 1.18, d, J = 6 |
| 47 | 18.94 | CH3 | 0.97, d, J = 7.5 |
| 48 | 18.86 | CH3 | 0.99, d, J = 7.5 |
| 49 | 18.60 | CH3 | 1.11, d, J = 7 |
| 50 | 15.80 | CH3 | 1.56, brs |
| 51 | 11.80 | CH3 | 0.85, t, J = 7.5 |

*Proton chemical shifts where the signals were obscured due to overlap, type of multiplicity and coupling constant could not be accurately determined and, therefore, they are not listed.

Actinoplanic acid B (2):
  $[\alpha]_D^{25}$ 16.7 (C, 0.1.2, $CH_3OH$)
  FABMS (+) m/z 951 ([M+H]), 973 ([M+Na]), 989 ([M+K]). (−) m/z 949 ([M−H])
  HR-FAB: (+) 973.5526 (calcd. for $C_{51}H_{82}O_{16}$+Na: 973.5501).
  IR (ZnSe) $v_{max}$: 3600–2600 (broad), 2931, 1709, 1378, 1250, 1186, 971, 736 $cm^{-1}$.

TABLE 5

NMR Assigment of Actinoplanic acid B (2) in $CD_3OD$.

| # | δC | Type | δH* |
|---|----|------|-----|
| 1 | 216.03 | CO | |
| 2 | 180.0 | CO | |
| 3 | 176.82 | CO | |
| 4 | 176.80 | CO | |
| 5 | 175.08 | CO | |
| 6 | 175.05 | CO | |
| 7 | 173.1 | CO | |
| 8 | 172.9 | CO | |
| 9 | 137.4 | CH | 5.24, dd, 15.5, 8 |
| 10 | 133.97 | C | |
| 11 | 133.29 | C | |
| 12 | 132.90 | CH | 4.92 |
| 13 | 131.17 | CH | 4.91 |
| 14 | 130.07 | CH | 5.37, td, 15.5, 6.0 |
| 15 | 81.68 | CH | 3.05, dd, 8.5, 3 |
| 16 | 76.61 | CH | 4.83, quint, 6.5 |
| 17 | 73.03 | CH | 4.87 |
| 18 | 52.5 | CH | 2.57 |
| 19 | 49.26 | CH2 | 1.91, d, 7.5 |
| 20 | 42.56 | CH2 | 2.59, |
| 21 | 39.02 | CH | 2.27, m |
| 22 | 38.76 | CH | 3.16, quint, 6.5 |
| 23 | 38.71 | CH | 3.16, quint, 6.5 |
| 24 | 38.11 | CH | 2.03, quint, 7.0 S |
| 25 | 37.11 | CH | 2.52, m |
| 26 | 36.98 | CH | 1.52 |
| 27 | 36.76 | CH2 | 2.55 |
| | | | 2.70 |
| 28 | 36.68 | CH2 | 2.55 |
| | | | 2.70 |
| 29 | 36.19 | CH2 | 2.55 |
| | | | 2.70 |
| 30 | 36.15 | CH2 | 2.55 |
| | | | 2.70 |
| 31 | 36.03 | CH2 | 1.68, m |

TABLE 5-continued

NMR Assigment of Actinoplanic acid B (2) in CD$_3$OD.

| # | δC | Type | δH* |
|---|-----|------|-----|
| 32 | 34.96 | CH2 | 1.51, m |
| 33 | 34.83 | CH2 | 1.50, m |
| 34 | 34.16 | CH2 | 2.17, t, 7.5 |
| 35 | 33.88 | CH2 | 1.22, m |
|   |       |     | 1.34, m |
| 36 | 33.44 | CH2 | 1.98, dd, 6.5,6.5 |
| 37 | 33.27 | CH2 | 1.34, m |
|    |       |     | 1.63 |
| 38 | 31.87 | CH | 2.54, m |
| 39 | 30.59 | CH2 | 1.35, m |
| 40 | 26.59 | CH2 | 1.00, m |
|    |       |     | 1.30, m |
| 41 | 26.42 | CH2 | 1.41, m |
|    |       |     | 1.59, m |
| 42 | 25.82 | CH2 | 1.27, m |
|    |       |     | 1.36, m |
| 43 | 21.52 | CH3 | 0.96, d, 6.5 |
| 44 | 21.24 | CH3 | 0.86, d, 6.5 |
| 45 | 20.23 | CH3 | 1.19, d, 6.0 |
| 46 | 18.61 | CH3 | 1.12, d,7.0 |
| 47 | 18.05 | CH3 | 0.92, d, 6.5 |
| 48 | 17.85 | CH3 | 0.95, d, 6.5 |
| 49 | 16.79 | CH3 | 1.62, d, 1.0 |
| 50 | 16.63 | CH3 | 1.63, d, 1.0 |
| 51 | 11.84 | CH3 | 0.86, t, 7.5 |

*Proton chemical shifts where the signals were obscured due to overlap, type of multiplicity and coupling constant could not be accurately determined and, therefore, they are not listed.

EXAMPLE 5

Actinoplanic acid A tetramethyl ester (3):

To a cooled (0° C.) solution of actinoplanic acid A from Example 3 (2.7 mg) in methylene chloride (0.5 mL) and methanol (0.05 mL) was added an excess of an ethereal solution of diazomethane. The solution was maintained at 0° C. for 4 hrs and solvents were evaporated under a stream of nitrogen to give the clean tetramethyl ester as a gum.

CI-MS (m/z): 1005 ([M+H]).

IR (ZnSe) $v_{max}$: 2931, 1736, 1439, 1250, 1168 cm$^{-1}$.

EXAMPLE 6

Actinoplanic acid B pentamethyl ester (4):

To a cooled (0° C.) solution of actinoplanic acid B from Example 3 (3.5 mg) in methylene chloride (0.5 mL) and methanol (0.05 mL) was added an excess of an ethereal solution of diazomethane. The solution was maintained at 0° C. for 4 hrs and solvents were evaporated under a stream of nitrogen to give the clean pentamethyl ester as a gum.

CI-MS (m/z): 1021 ([M+H]).

IR (ZnSe) $v_{max}$: 3536, 2955, 1734, 1438, 1375, 1250, 1200, 1167, 972 cm$^{-1}$.

EXAMPLE 7

In vitro inhibition of ras farnesyl transferase

Human FPTase was expressed in *Escherichia coli* and then the recombinant protein was purified as described by Omer, et al., Biochemistry 32, 5167 (1993). The assay was performed in a volume of 100 μl containing 100 mM N-(2-hydroxy ethyl) piperazine-N'-(2-ethane sulfonic acid) (HEPES), pH 7.5, 5 mM MgCl$_2$, 5 mM dithiothreitol (DTT), 10 μM ZnCl$_2$, 0.1% (w/v) polyethylene glycol 20,000, 50 nM [3H]-Farnesyl Pyrophosphate ([3H]-FPP, 740 CBq/mmol, NEN-DuPont), 0.1 μM ras-CVIM and 2 μg of human recombinant farnesyl-protein transferase. The assay was run in the presence of the compound(s) for 30 minutes at 31° C. and then quenched by placing the tubes in an ice bath for 5 minutes. Trichloracetic acid (TCA, 0.1 ml of 30% (v/v) in ethanol followed by 50 μl of 0.25% (w/v) Bovine Serum Albumin in water was added to the tubes, vortexed for 5 minutes then placed in a 37° C. water bath for 30 minutes to facilitate the hydrolysis of the unused farnesyl pyrophosphate. The precipitate was collected on a Packard double thickness filtermat, using a Tomtec Mach II Cell Harvester and washed with 8 ml of 100% Ethanol. The filtermats were dried in a microwave oven and counted in a LKB Betaplate counter. The compounds were dissolved in dimethyl sulfoxide and were diluted 20-fold into the assay.

TABLE 6

Inhibition of RAS farnesylation by compounds of this invention*

| Compound | LC$_{50}$ (nM)* |
|---|---|
| 1 | 230 nM |
| 2 | 50 nM |

*(IC$_{50}$ is the concentration of the test compound which gives 50% inhibition of FPTase under the described assay conditions)

What is claimed is:

1. A compound which inhibits farnesyl-protein transferase of the formula I:

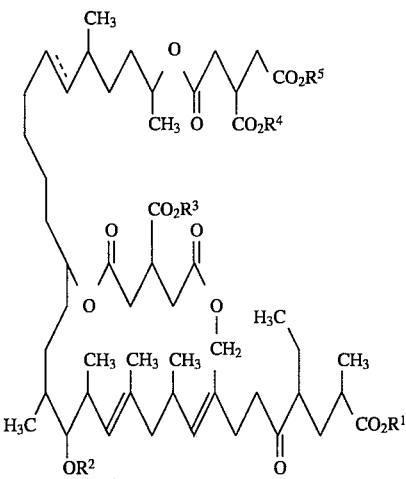

wherein:

R$^1$, R$^3$, R$^4$ and R$^5$ are independently selected from:
  a) hydrogen;
  b) C$_{1-5}$ alkyl; and
  c) C$_{1-5}$ alkyl substituted wth a member of the group consisting of:
    i) phenyl,
    ii) phenyl substituted with methyl, methoxy, halogen (Cl, Br, F, I) or hydroxy; and R$^2$ is selected from hydrogen, C$_{1-4}$ alkyl, benzoyl or acetyl;

wherein the dashed line represents the presence of a second bond, which results in a double bond, or the absence of a second bond; and wherein at least two R$^1$, R$^3$, R$^4$ or R$^5$ are hydrogen; or a pharmaceutically acceptable salt thereof.

2. A compound which inhibits farnesyl-protein transferase of the formula II:

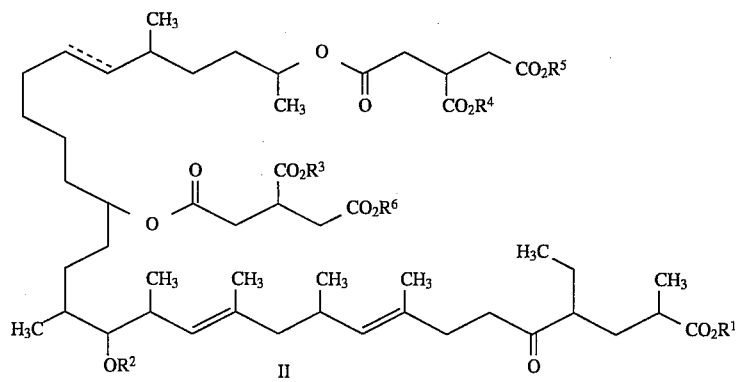

II wherein:

R¹, R³, R⁴, R⁵ and R⁶ are independently selected from:
a) hydrogen;
b) $C_{1-5}$ alkyl; and
c) $C_{1-5}$ alkyl substituted wth a member of the group consisting of:
i) phenyl,
ii) phenyl substituted with methyl, methoxy, halogen (Cl, Br, F, I) or hydroxy; and R² is selected from hydrogen, $C_{1-4}$ alkyl, benzoyl or acetyl;

wherein the dashed line represents the presence of a second bond, which results in a double bond, or the absence of a second bond; and wherein at least two R¹, R³, R⁴ or R⁵ are hydrogen;
or a pharmaceutically acceptable salt thereof.

3. A prodrug of a compound which inhibits farnesyl-protein transferase of the formula I:

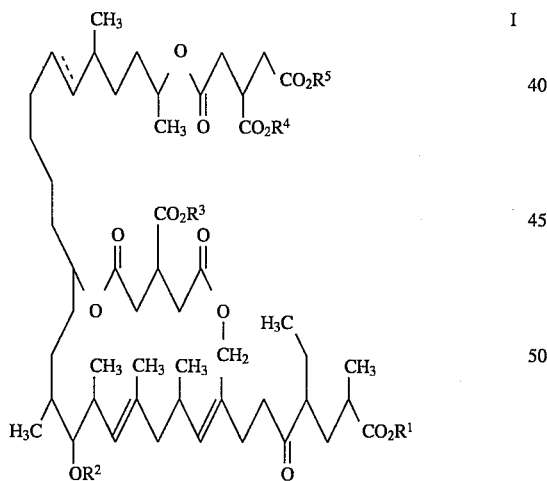

I wherein:

R¹, R³, R⁴ and R⁵ are independently selected from:
a) hydrogen;
b) $C_{1-5}$ alkyl; and
c) $C_{1-5}$ alkyl substituted wth a member of the group consisting of:
i) phenyl,
ii) phenyl substituted with methyl, methoxy, halogen (Cl, Br, F, I) or hydroxy;

R² is selected from hydrogen, $C_{1-4}$ alkyl, benzoyl or acetyl; provided either one or none of R¹, R³, R⁴ or R⁵ is hydrogen; and wherein the dashed line represents the presence of a second bond, which results in a double bond, or the absence of a second bond.

4. A prodrug of a compound which inhibits farnesyl-protein transferase of the formula II:

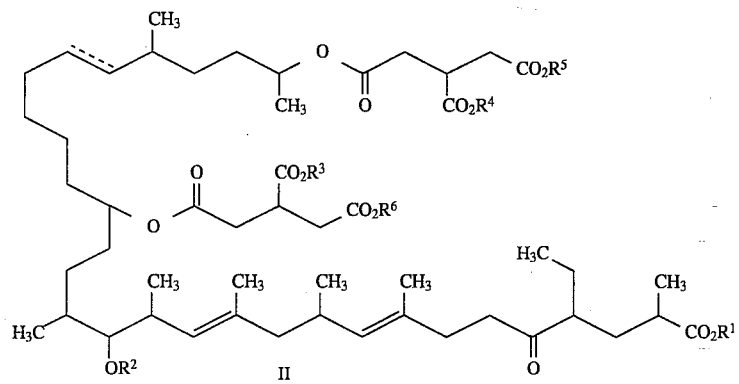

wherein:
$R^1$, $R^3$, $R^4$, $R^5$ and $R^6$ are independently selected from:
a) hydrogen;
b) $C_{1-5}$ alkyl; and
c) $C_{1-5}$ alkyl substituted wth a member of the group consisting of:
  i) phenyl,
  ii) phenyl substituted with methyl, methoxy, halogen (Cl, Br, F, I) or hydroxy;

$R^2$ is selected from hydrogen, $C_{1-4}$ alkyl, benzoyl or acetyl; provided either one or none of $R^1$, $R^3$, $R^4$, $R^5$ or $R^6$ is hydrogen; and wherein the dashed line represents the presence of a second bond, which results in a double bond, or the absence of a second bond.

5. The compound according to claim 1 of the formula Ia:

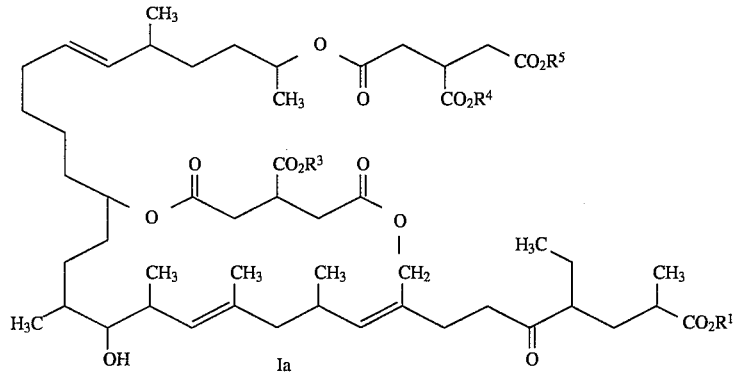

wherein:
$R^1$, $R^3$, $R^4$ and $R^5$ are independently selected from:

a) hydrogen;
b) $C_{1-5}$ alkyl; and
c) $C_{1-5}$ alkyl substituted wth a member of the group consisting of:
  i) phenyl,
  ii) phenyl substituted with methyl, methoxy, halogen (Cl, Br, F, I) or hydroxy; and wherein at least $R^4$ and $R^5$ are hydrogen;
or a pharmaceutically acceptable salt thereof.

6. The compound according to claim 2 of the formula IIa:

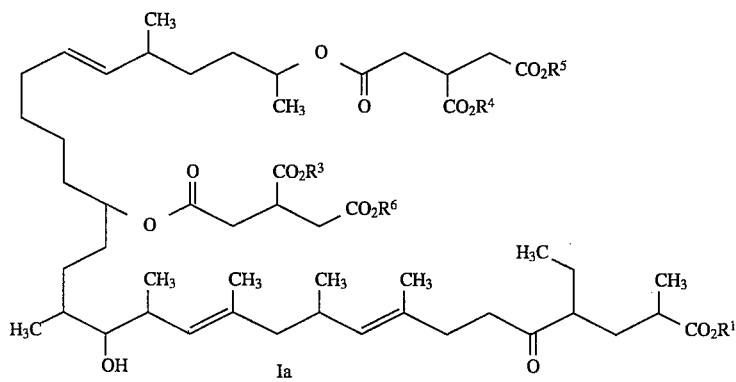

wherein:
R$^1$, R$^3$, R$^4$, R$^5$ and R$^6$ are independently selected from:
a) hydrogen;
b) C$_{1-5}$ alkyl; and
c) C$_{1-5}$ alkyl substituted wth a member of the group consisting of:
i) phenyl,
ii) phenyl substituted with methyl, methoxy, halogen (Cl, Br, F, I) or hydroxy; and wherein at least R$^6$ and R$^3$ are hydrogen or R$^4$ and R$^5$ are hydrogen or R$^3$, R$^4$, R$^5$ and R$^6$ are hydrogen;
or a pharmaceutically acceptable salt thereof.

7. The prodrug according to claim 3 of the formula Ia:

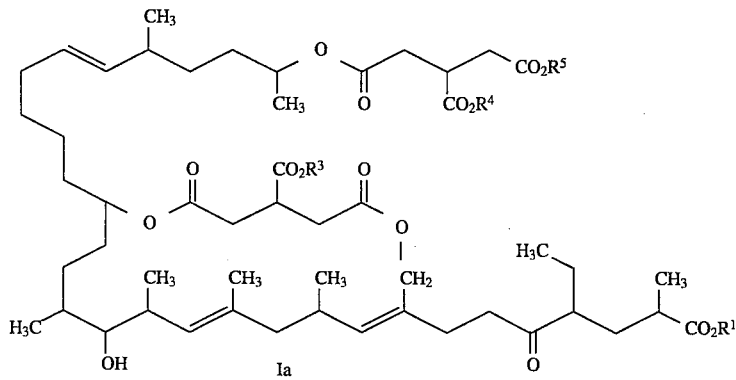

wherein:

R$^1$, R$^3$, R$^4$, R$^5$ and R$^6$ are independently selected from:
a) C$_{1-5}$ alkyl; and
b) C$_{1-5}$ alkyl substituted wth a member of the group consisting of:
i) phenyl,
ii) phenyl substituted with methyl, methoxy, halogen (Cl, Br, F, I) or hydroxy.

8. The prodrug according to Claim 4 of the formula IIa:

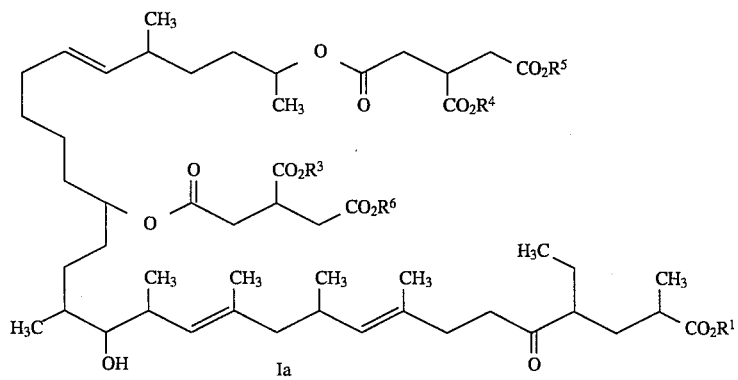

wherein:

R$^1$, R$^3$, R$^4$, R$^5$ and R$^6$ are independently selected from:
a) C$_{1-5}$ alkyl; and
b) C$_{1-5}$ alkyl substituted wth a member of the group consisting of:
  i) phenyl,
  ii) phenyl substituted with methyl, methoxy, halogen (Cl, Br, F, I) or hydroxy.

9. The compound according to claim 1 which is:

1,2,3-propanetricarboxylic acid 1-[10-[4-carboxy-19-(6-carboxy-4-ethyl- 3-oxoheptyl)-12-hydroxy-11,13,15, 17-tetramethyl-2,6-dioxo-1,7-dioxacycloeiocosa-14,18-dien-8-yl]-1,4-dimethyl-5-decenyl]ester;

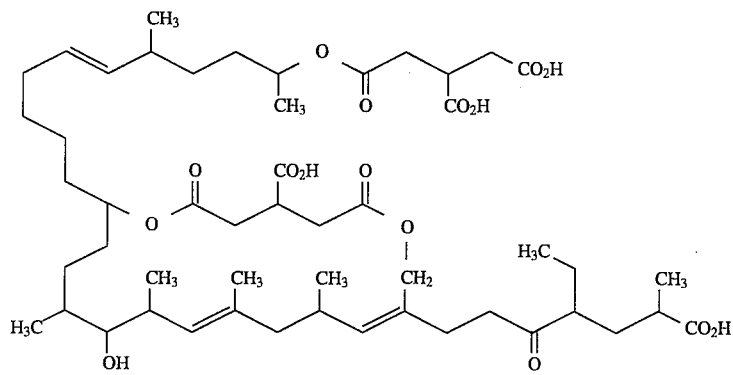

or a pharmaceutically acceptable salt thereof.

10. The compound according to claim 2 which is:

1,2,3-propanetricarboxylic acid 1-[28-carboxy-11-[[3,4-dicarboxy-1-oxopentyl]oxy]- 26-ethyl-15-hydroxy-1, 4,14,16,18,20,22-heptamethyl- 25-oxo-5,17,21-nonacosatrienyl]ester;

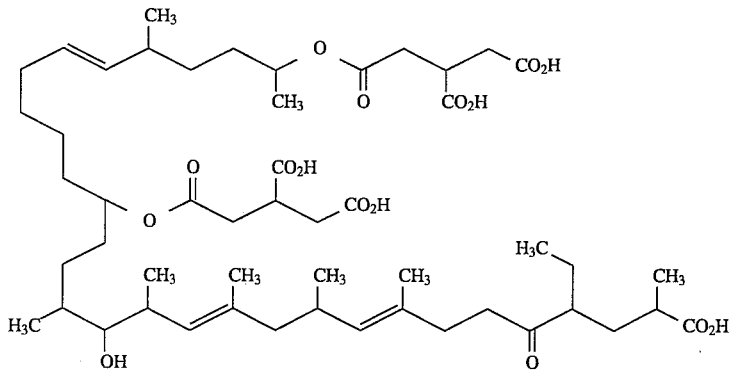

or a pharmaceutically acceptable salt thereof.

11. The prodrug according to claim 3 which is:

1,2,3-propanetricarboxylic acid 1-[10-[19-(4-ethyl-7-methoxy-6-methyl- 3,7-dioxoheptyl)-12-hydroxy-11, 13,15,17-tetramethyl-4-(methoxycarbonyl)- 2,6-dioxo-1,7-dioxacycloeiocosa-14,18-dien-8-yl}-1,4-dimethyl-5-decenyl]2,3-dimethyl ester

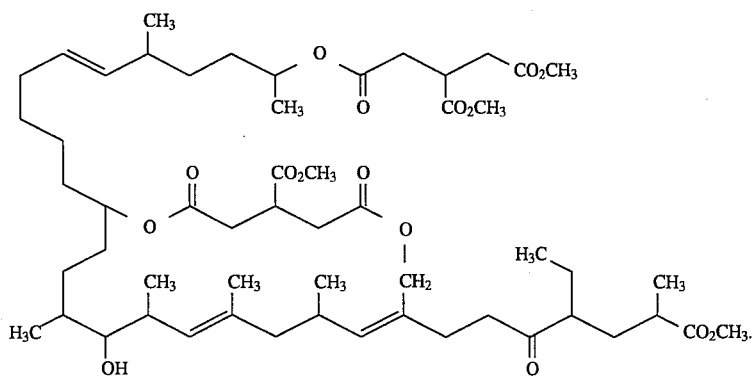

3

12. The prodrug according to claim 4 which is:

1,2,3-propanetricarboxylic acid 1-[26-ethyl-15-hydroxy-29-methoxy-11-[[ 5-methoxy-3-(methoxycarbonyl)-1,5-dioxopentyl[oxy]-1,4,14,16,18,20,22,28-octamethyl-25,29-dioxo-5,17,21-nonacosatrienyl]] 2,3-dimethyl ester

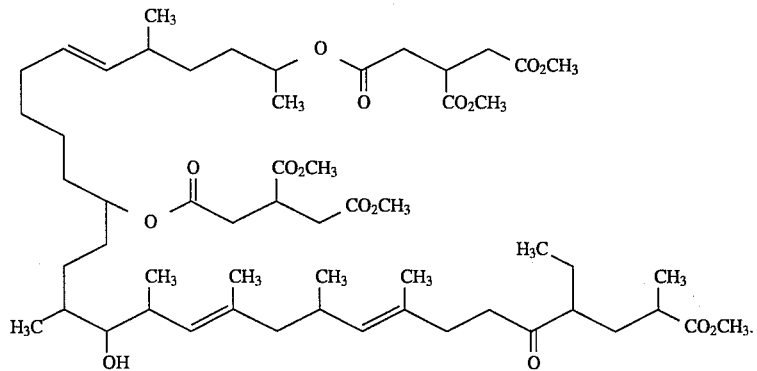

4

13. A pharmaceutical composition comprising a pharmaceutical carrier, and dispersed therein, a therapeutically effective amount of a compound of claim 1.

14. A pharmaceutical composition comprising a pharmaceutical carrier, and dispersed therein, a therapeutically effective amount of a compound of claim 2.

15. A pharmaceutical composition comprising a pharmaceutical carrier, and dispersed therein, a therapeutically effective amount of a compound of claim 3.

16. A pharmaceutical composition comprising a pharmaceutical carrier, and dispersed therein, a therapeutically effective amount of a compound of claim 4.

17. A method for inhibiting farnesyl-protein transferase which comprises administering to a mammal in need thereof a therapeutically effective amount of a composition of claim 13.

18. A method for inhibiting farnesyl-protein transferase which comprises administering to a mammal in need thereof a therapeutically effective amount of a composition of claim 14.

19. A method for inhibiting farnesyl-protein transferase which comprises administering to a mammal in need thereof a therapeutically effective amount of a composition of claim 15.

20. A method for inhibiting farnesyl-protein transferase which comprises administering to a mammal in need thereof a therapeutically effective amount of a composition of claim 16.

* * * * *

UNITED STATES PATENT AND TRADEMARK OFFICE
CERTIFICATE OF CORRECTION

PATENT NO. : 5,510,371

DATED : Apr. 23, 1996

INVENTOR(S) : Sheo B. Singh, George M. Garrity, Olga Genilloured, Russell B. Lingham, Isabel Martin, Mary N. Omstead, Keith C. Silverman and Deborah L. Zink It is certified that error appears in the above-identified patent and that said Letters Patent is hereby corrected as shown below:

At Column 28, Claim 3, line 24 should read as follows:

c) C1-5 alkyl substituted with a member of the group consisting of:

At Column 31, Claim 6, after the structure should read as follows:

IIa

At Column 32, Claim 8, after the structure should read as follows:

IIa

Signed and Sealed this

Tenth Day of September, 1996

Attest:

BRUCE LEHMAN

*Attesting Officer*          *Commissioner of Patents and Trademarks*